United States Patent
Niemann et al.

(10) Patent No.: US 9,322,952 B2
(45) Date of Patent: Apr. 26, 2016

(54) METHOD AND DEVICE FOR DETECTING RAIN ON A WINDSHIELD

(71) Applicant: Hella KGaA Hueck & Co., Lippstadt (DE)

(72) Inventors: Thomas Niemann, Delmenhorst (DE); Olaf Lüdtke, Vollersode (DE); Almut Schlarmann, Bremen (DE); Jürgen Palloks, Westerstede (DE); Cevin Czsich, Bremen (DE); Jörg Stürmann, Bremen (DE)

(73) Assignee: HELLA KGAA HUECK & CO., Lippstadt (DE)

( * ) Notice: Subject to any disclaimer, the term of this patent is extended or adjusted under 35 U.S.C. 154(b) by 399 days.

(21) Appl. No.: 13/712,058

(22) Filed: Dec. 12, 2012

(65) Prior Publication Data

US 2013/0145839 A1 Jun. 13, 2013

(30) Foreign Application Priority Data

Dec. 12, 2011 (DE) .......................... 10 2011 120 867

(51) Int. Cl.
*G01N 11/00* (2006.01)
*G01W 1/14* (2006.01)
*B60S 1/08* (2006.01)

(52) U.S. Cl.
CPC ................ *G01W 1/14* (2013.01); *B60S 1/0859* (2013.01)

(58) Field of Classification Search
CPC .............. G01N 29/00; G01N 29/2437; G01N 29/2443; G01N 29/245; G01N 21/17; B60S 1/0491; B60S 1/0859; B60S 1/0855; B60S 1/0833; B60S 1/0818
USPC ............................ 73/579, 597, 598, 645, 646
See application file for complete search history.

(56) References Cited

U.S. PATENT DOCUMENTS

| 4,665,351 | A | | 5/1987 | Nyberg | |
|---|---|---|---|---|---|
| 5,119,002 | A | * | 6/1992 | Kato et al. | ..................... 318/444 |
| 5,278,620 | A | * | 1/1994 | Godlove | ............ G03G 21/0011 15/256.5 |
| 5,703,568 | A | * | 12/1997 | Hegyi | ........................... 340/602 |
| 5,773,946 | A | * | 6/1998 | Montero | ............... B60S 1/0859 318/460 |

(Continued)

FOREIGN PATENT DOCUMENTS

| CN | 101339124 A | 1/2009 |
|---|---|---|
| DE | 3910116 | 1/1990 |

(Continued)

OTHER PUBLICATIONS

Disclosed anonymously, Piezoelectric anti-chatter windshield wiper blade, Jan. 1993, Research Disclosure database No. 345095, p. 1-2.*

(Continued)

*Primary Examiner* — Hezron E Williams
*Assistant Examiner* — Truong Phan
(74) *Attorney, Agent, or Firm* — Muncy, Geissler, Olds & Lowe, P.C.

(57) ABSTRACT

In a method for detecting rain on a windshield, whose degree of wetting is determined with at least one sensor value, it is provided that the sensor value is determined piezoelectrically, wherein vibrations on the windshield are detected, which change depending on the degree of wetting or raindrops hitting the windshield. As a result, the entire windshield serves as a detection surface, thereby yielding a high accuracy.

3 Claims, 1 Drawing Sheet

(56) References Cited

U.S. PATENT DOCUMENTS

| | | | |
|---|---|---|---|
| 2005/0046372 A1* | 3/2005 | Heo | 318/483 |
| 2005/0125109 A1* | 6/2005 | Hayashi | H02G 3/081 |
| | | | 701/1 |
| 2006/0241834 A1* | 10/2006 | Kithil | B60R 21/013 |
| | | | 701/45 |

FOREIGN PATENT DOCUMENTS

| | | | | |
|---|---|---|---|---|
| DE | 0930207 | * | 1/1998 | B60S 1/0491 |
| DE | 0930207 A2 | * | 1/1998 | B60S 1/0491 |
| DE | 19805724 | | 8/1998 | |
| DE | 102004018219 | * | 11/2005 | |
| DE | 102004061219 | * | 3/2007 | |
| DE | 102007002257 | | 7/2008 | |
| WO | WO9919185 | | 4/1999 | |

OTHER PUBLICATIONS

Jayant Sirohi, Fundamental Understanding of Piezoelectric Strain Sensors, Apr. 2000, Journal of Intelligent Material Systems and Structures, vol. 11, p. 1.*

* cited by examiner

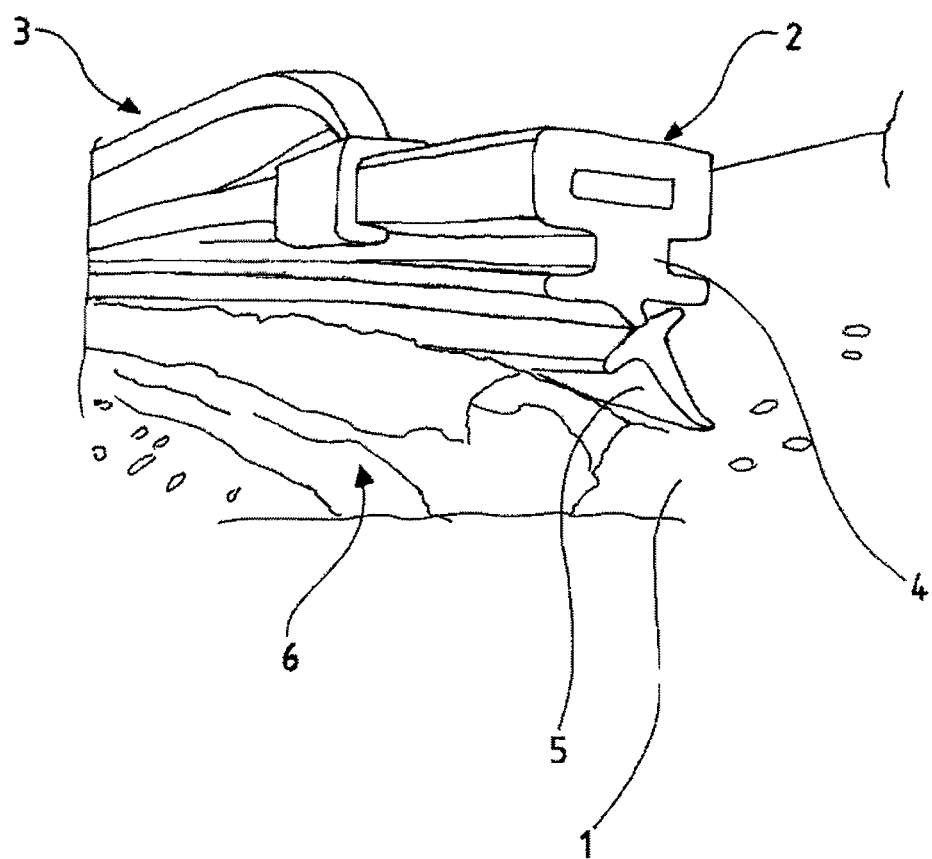

METHOD AND DEVICE FOR DETECTING RAIN ON A WINDSHIELD

CROSS-REFERENCE TO RELATED APPLICATIONS

This application claims priority of Application No. 10 2011 120 867.8 filed in Germany on Dec. 12, 2011 under 35 U.S.C. §119, the entire contents of which are hereby incorporated by reference.

BACKGROUND OF THE INVENTION

1. Field of the Invention

The invention relates to a method for detecting rain on a windshield, whose degree of wetting is determined with at least one sensor value. In addition, the invention also relates to a device for detecting rain on a windshield, with at least one rain sensor, which is allocated to a windshield wiper system for the windshield, and a motor vehicle with such a device.

2. Brief Discussion of the Related Art

In motor vehicles, rain sensors are most often coupled with an activation of the windshield wiper system, so that once rain hitting the windshield has been registered or a predetermined degree of windshield wetting has been detected, windshield wipers are automatically activated. The most common rain sensors today are those based on optoelectric measurement. These rain sensors most often exhibit at least one light source and at least one detecting photodiode, wherein the light source sends out an optical signal, which is reflected in a predetermined detection range on the windshield, and the reflected optical signal is detected by the photodiode. A differential value is then derived from the transmitted and detected optical signal, based upon which the degree of wetting for the detection range of the windshield is determined. However, the disadvantage is that the detection range of the optoelectric rain sensors only detects a small section usually measuring about 2 cm$^2$ of the windshield. Therefore, rain is inaccurately detected primarily at the beginning of showers, since a larger amount of rain might already have hit the windshield without the detection range having been sufficiently wetted. In addition, the spray from oncoming traffic is only inadequately detected, if at all.

BRIEF SUMMARY OF THE INVENTION

Therefore, the object of the invention is to develop a rain sensor having a large surface as the detection range, and a higher accuracy with respect to the degree of wetting to be detected.

In terms of the method, the degree of wetting is determined with at least one sensor value. The sensor value is determined piezoelectrically, and vibrations on the windshield are detected. The change depends on the degree of wetting or raindrops hitting the windshield, and the vibrations on the windshield are detected via at least one wiper blade of a windshield wiper system and its coupling to the windshield.

In terms of the device, the device includes at least one rain sensor, which is allocated to the windshield wiper system of the windshield. The rain sensor exhibits at least one piezo element, and the windshield wiper system has at least one wiper blade. The wiper blade has the piezo element of the rain sensor.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

The sole FIGURE illustrates a windshield wiper system, in accordance with the present invention.

DETAILED DISCUSSION OF THE PREFERRED EMBODIMENTS

In the method for detecting rain on a windshield, whose degree of wetting is detected with at least one sensor value, the invention provides that the sensor value is determined piezoelectrically, wherein vibrations on the windshield are detected, which change depending on the degree of wetting or raindrops hitting the windshield.

According to the invention, the vibrations on the windshield are detected via at least one wiper blade of a windshield wiper system and its coupling to the windshield. The detection takes place by means of a piezoelectric element arranged in the wiper blade.

In particular, a changing amplitude in windshield vibration is detected and evaluated. The windshield typically vibrates at a characteristic frequency. In a preferred embodiment of the invention, amplitude patterns intended for different environmental conditions are stored in a file. These stored amplitude patterns are compared with the measured amplitude progressions. Based on the deviations and in particular slight deviations from the stored patterns, a conclusion can then be reached about a specific type of environmental conditions, e.g., light rain, strong rain or spray. A corresponding windshield wiper control action can be derived from this. As a consequence, the detection range for recognizing rain advantageously extends over the entire windshield, so that even a few raindrops are recognized with a high degree of certainty, regardless of where they hit the windshield, with the same even holding true for spray that only hits a section of the windshield. The degree of windshield wetting is here detected by way of the windshield vibrations triggered by the rain or spray, wherein a sensor value is piezoelectrically recorded, and used for comparison to a stored vibration profile.

Therefore, the degree of wetting, for example when water and/or similar liquids are present on the windshield, can be determined regardless of any other dirt on the windshield, which had previously often led to malfunctions while detecting the degree of wetting.

Depending on the determined sensor value, a windshield wiper system allocated to the windshield is then activated once a predetermined sensor value has been reached. The windshield wiper system can wipe the windshield at intervals or continuously, depending on the intensity of the recognized degree of wetting or incident raindrops. By contrast, spray hitting the windshield generates a vibration profile to be differentiated from that associated with raindrops, so that a single wipe of the windshield could then take place, for example. The vibration profiles differ primarily in terms of their amplitude progression and the strength of the respective vibration amplitudes. The windshield vibrations can be evaluated especially precisely by generating a distribution profile for the degree of wetting given at least two sensor values detected at locations spaced apart from each other. For example, this makes it possible to localize spray that only hits a section of the windshield.

It can also be provided that at least one additional sensor value is detected, wherein an optical signal is sent out, the optical signal is reflected on the windshield in a predetermined detection range, the reflected optical signal is detected, and a differential value is derived from the transmitted and detected signal, based upon which the degree of wetting is determined for the windshield. Rain can be recognized with a high degree of certainty using the additional sensor value, since two varyingly configured sensor systems detect the degree of windshield wetting. The sensor values detected in different ways can also be linked with a targeted control of the windshield wiper system. For example, if rain is recognized only with the piezoelectrically recorded sensor value based on corresponding vibrations, without rain being recognized with the optoelectric sensor value, the windshield can be wiped just once for the time being. When the windshield wiper system is activated for the first time, it is here advantageously provided that the area of the windshield in which the optical signal is reflected be wiped especially slowly, and any water located on the windshield be determined and quantified with the optical signal in the wiping process. In this way, the optoelectric sensor value enables a capacitive measurement of water located on the pane. In combination with the vibrations determined over a predetermined measuring period, various states or degrees of wetting can be differentiated from each other, thereby always ensuring optimal control in the wiping process, and hence an optimal view through the windshield.

In another embodiment, the sensor value can also be used for automatic headlight control, so as to account for visibility and light conditions, which are often poor in the rain.

The invention further relates to a device for detecting rain on a windshield with at least one rain sensor, which is allocated to a windshield wiper system of the windshield, and distinguished by the fact that the rain sensor exhibits at least one piezo element. The piezo element detects windshield vibrations, wherein steady rain, isolated raindrops or spray from oncoming traffic have vibration profiles that vary from both one another and other factors that cause vibrations. These vibrations or vibration profiles then cause the respective piezo element to become specifically coupled to the windshield. It is precisely this coupling of the piezo element to the windshield which is here detected by the piezo element. In a dry state, the piezo element exhibits a higher acoustic coupling to the windshield, so that the vibrations are intensely reflected. By contrast, the piezo element exhibits a lower acoustic coupling to the windshield in a wet state.

In order to detect the vibrations as directly as possible, it is provided that the piezo element of the rain sensor be arranged on the outside of the windshield. The arrangement according to the invention for the piezo element stems from the fact that the windshield wiper system has at least one wiper blade, and the wiper blade has the piezo element of the rain sensor. The piezo element can thus be allocated to the windshield without any significant added structural outlay, thereby yielding a particularly inexpensive arrangement. In addition, the rain sensor is easy to install on a windshield after the fact.

Arranging the piezo element in a rubber section of the wiper blade ensures that the piezo element abuts the pane as closely as possible, wherein the piezo element is at the same time optimally protected relative to the environment. This prevents any damage to the piezo element. In addition, arranging the piezo element in the wiper blade makes it possible to determine wear on the wiper blade, since the coupling of the piezo element to the windshield also changes as a function of wiper blade wear.

A preferred embodiment here provides that the piezo element be designed as a piezoelectric line, which detects the wiper blade over its entire longitudinal expansion. As a consequence, the piezo element extends over as large an area or a large surface of the windshield, making it possible to recognize and potentially also localize vibrations with a high level of accuracy. For example, vibrations exerting a different effect could be used at opposing ends of the piezo element in order to establish a distribution profile for the degree of windshield wetting. In particular, motor vehicles most often have two wiper blades allocated to a windshield, so that each wiper blade preferably exhibits a piezo element, and the most uniform possible distribution of piezo elements is achieved over the entire windshield area.

In order to help prevent the wiper blades from sticking or freezing to the windshield during a frost, it is further provided that the piezo element has a heatable design. Whether or even when the piezo element is heated is here in turn determined by the vibrations or specific coupling to the windshield. Heating also makes it possible to minimize wear on the wiper blade.

The measuring behaviour of the rain sensor can be improved by having it also exhibit at least one additional, optoelectric sensor unit.

The invention further relates to a motor vehicle, which exhibits the device described above.

The invention will be explained below based on an exemplary embodiment depicted in the drawing.

The drawing presents a detailed view of a windshield 1 with a wiper blade 2 of a windshield wiper system 3. This wiper blade 2 has a guide section 4 along with a rubber section 5 moveably held on the guide section 4. The rubber section 5 is guided along the windshield 1, pushing away any water 6 located on the windshield 1. A piezo element is integrated into the rubber section 5 of the wiper blade 2. The piezo element is used to determine the coupling of the wiper blade 2 to the windshield 1, and the windshield wiper system 3 is activated once a predetermined degree of wetting has been detected.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A method for detecting rain on a windshield, comprising:
    detecting vibrations on the windshield, caused by rain, with a piezoelectric sensor, the vibrations being detected via at least one wiper blade of a windshield wiper system, and via a coupling between the at least one wiper blade and the windshield,
    determining a sensor value from the output of the piezoelectric sensor, which depends on the degree of wetting or raindrops hitting the windshield,
    comparing the sensor value with known vibration profiles, and
    determining the environmental condition on the windshield, caused by the rain, from said comparing;
    wherein at least one additional sensor value is detected, wherein an optical signal is sent out, the optical signal is reflected on the windshield in a predetermined detection range, the reflected optical signal is detected, and a differential value is derived from the transmitted and detected signal, based upon which the degree of wetting is determined for the windshield.

2. A method for detecting rain on a windshield, whose degree of wetting is determined with at least one sensor value:
- wherein the sensor value is determined piezoelectrically, wherein vibrations on the windshield are detected, which change depending on the degree of wetting or raindrops hitting the windshield, and that the vibrations on the windshield are detected via at least one wiper blade of a windshield wiper system and its coupling to the windshield;
- wherein at least one additional sensor value is detected, wherein an optical signal is sent out, the optical signal is reflected on the windshield in a predetermined detection range, the reflected optical signal is detected, and a differential value is derived from the transmitted and detected signal, based upon which the degree of wetting is determined for the windshield;
- wherein, when the windshield wiper system is activated for the first time, the area of the windshield in which the optical signal is reflected is wiped especially slowly, and any water located on the windshield is determined and quantified with the optical signal in the wiping process.

3. A device for detecting rain on a windshield, comprising:
- a windshield wiper system of the windshield,
- at least one wiper blade included in said windshield wiper system,
- at least one rain sensor included in the windshield wiper system includes at least one piezo element,
- the at least one wiper blade includes one of the at least one rain sensors having the at least one piezo element, with the piezo element being coupled to the windshield through the wiper blade, and
- an output of the piezo element is compared to stored vibration profiles to determine the environmental condition on the windshield caused by rain;
- wherein the at least one rain sensor includes at least one additional, optoelectric sensor unit.

* * * * *